United States Patent [19]
Anderson et al.

[11] Patent Number: 5,384,031
[45] Date of Patent: Jan. 24, 1995

[54] REFERENCE ELECTRODE

[75] Inventors: Carter Anderson, Eagan; Kee V. Sin, Lino Lakes, both of Minn.

[73] Assignee: Diametrics Medical, Inc., Roseville, Minn.

[21] Appl. No.: 980,086

[22] Filed: Nov. 24, 1992

Related U.S. Application Data

[63] Continuation-in-part of Ser. No. 875,308, Apr. 29, 1992, abandoned.

[51] Int. Cl.⁶ ............... G01N 27/333; G01N 27/401
[52] U.S. Cl. ........................... 204/435; 204/416; 427/58
[58] Field of Search ............ 204/416, 418, 419, 435

[56] References Cited

U.S. PATENT DOCUMENTS

| | | | |
|---|---|---|---|
| 3,117,070 | 11/1967 | Anderson | 204/196 |
| 3,700,579 | 10/1972 | Clifton et al. | 204/415 |
| 3,787,307 | 1/1974 | Schwab et al. | 204/420 |
| 4,454,007 | 6/1984 | Pace | 204/435 |
| 4,571,292 | 2/1986 | Liu et al. | 204/412 |
| 4,734,184 | 3/1988 | Burleigh et al. | 204/409 |
| 4,816,132 | 3/1989 | Kotani et al. | 204/435 |
| 4,891,125 | 1/1990 | Schultz | 204/435 |
| 4,913,793 | 4/1990 | Leonard | 204/435 |
| 4,933,048 | 6/1990 | Lauks | 204/416 |
| 5,037,527 | 8/1991 | Hayashi et al. | 204/435 |
| 5,066,383 | 11/1991 | Yamaguchi et al. | 204/435 |
| 5,071,537 | 12/1991 | Yamaguchi et al. | 204/435 |

OTHER PUBLICATIONS

Dohner et al, "Reference Electrode with Free-Flowing Free-Diffusion Liquid Junction", Anal. Chem., 58:2585–2589 (1986).

Bettelheim, A. et al, "A New Polymer Ag/AgCl Reference Electrode for Electrochemistry with No Contacting Electrolyte Solution", J. Electrochem. Soc.: Accelerated Brief Communication, pp. 1041–1042 (Apr. 1988).

Maas, A. H. J., "Effects of the Liquid Junction on pH Measurement in Blood; the 0.160 Mol/L Sodium Chloride Bridge", National Bureau of Standards Special Publication 450, Proceedings of a Workshop on pH and Blood Gases held in Gaithersburg, Md., Jul. 7–8, 1975. Issued Jun. 1977.

"An Introduction to Electroanalytical Chemistry", Principles of Instrumental Analysis, Second Edition, pp. 531–534 (1980)* month unavailable.

Primary Examiner—T. Tung
Attorney, Agent, or Firm—Haugen and Nikolai

[57] ABSTRACT

A reference electrode system for a disposable test cell which provides both a reference electrical potential and a liquid junction between the reference medium and an analytic or sample medium to which a sample is introduced to be tested includes a substrate carrying and supporting a thin metallic electrode layer, an hydrophilic medium overlays the electrodes, a portion connecting the metallic layer and the sample conducting medium to provide an electrical connection and free diffusion liquid junction with the sample medium, a liquid impermeable dielectric barrier layer sealing all but a selected, relatively minor portion of the hydrophilic medium exposed to contact the analytic medium. Electrolyte salts introduced into the free diffusion channel control both the reference electrode potential and the junction potential.

22 Claims, 4 Drawing Sheets

REFERENCE ELECTRODE

CROSS-REFERENCE TO RELATED APPLICATION

This patent application is a continuation-in-part of copending application Ser. No. 07/875,308, filed Apr. 29, 1992, now abandoned.

BACKGROUND OF THE INVENTION

I. Field of the Invention

The present invention is related generally to electrochemical cells and to devices and methods for electrochemically determining the concentrations of one or more desired species of interest in a sample solution. More particularly, the invention is directed to a new planar, free diffusion reference electrode or reference half cell for use in combination with one or more additional electrodes making up a sample analyzing or sensor half cell used to make quantitative concentration determinations.

II. Related Art

Methods and devices utilized for determining concentration of electroactive species in solution using electrochemical or electrolytic methods such as, for example, the determination of pH, $pCO_2$ and electrolytes in blood samples, are well known. These instruments typically include a pair of electrochemical half cells, one of which is used as the sensor or sample analyzing half cell and the other as a reference electrode or reference half cell. The sensor half cell is normally provided with a membrane which forms complexes with the specific ion or ions to be measured in the sample. A voltage or potential is developed across the membrane that is proportional to the concentration of the species of interest in the sample. Generally, in accordance with the Nernst equation, by knowing the ion concentration of the species of interest on the internal side of the sensor membrane and measuring the potential across the membrane, it is possible to readily determine the unknown ion concentration on the opposite (sample) side of the membrane.

Theoretically, to make an accurate measurement, the reference half cell must maintain a constant potential. It is typically a metal/metal salt couple in equilibrium with the anions of the salt materials such as silver/silver chloride (Ag/AgCl) in equilibrium with chloride ions ($Cl^-$). The stability of the reference half cell potential depends on the stability of the anion concentration in the reference half cell electrolyte medium. It is used with the sample measurement electrode to complete the electrical circuit through the sample.

The reference electrode or half cell is generally constructed similar to the sensor half cell, except that, whereas the membrane separating the electrode itself from the sample solution in the case of the sensor half cell is normally rather species-specific with respect to transport across the membrane, the material of the reference half cell is normally not specific to a particular species. Such materials as glass frits and various porous ceramic separator materials, or even small open weep holes, typically isolate the reference electrolyte medium from that of the sample or sensor half cell. Separation is such that mixing of the two is minimized. An additional technique involves an ion-conductive salt bridge or bridge electrolyte as the conduction mechanism to complete the electrical circuit between the reference half cell and the sensor or sample half cell.

Reference electrodes as typically constructed are relatively large and expensive, requiring many distinct components which are precision assembled. Such a reference electrode half cell is illustrated and described, for example, by Dohner et al in "Reference Electrode with Free-Flowing Free-Diffusion Liquid Junction", Anal. Chem., 58:2585-2589 (1986).

Present reference electrodes as typically constructed also contain large volumes (0.5-10 ml) of an internal electrolyte solution. The internal electrolyte and bridge solution defines the equilibrium potential of the electrode, and the junction potential created with introduction of the sample. In addition to being rather complicated and expensive to produce, the large number of pieces involved and the large volume of internal electrolyte solution make any change of the internal and bridge electrolyte a very difficult and time consuming task.

One significant problem with glass frit and other porous separator materials involves the clogging of the junction by high molecular weight contaminants. A clogged junction typically renders the reference electrode unsuitable or unusable because of drift or high impedance. This problem is particularly acute when the reference electrode is used in a device making measurements in biological solutions such as blood, plasma, or serum.

Another significant problem with glass frit and other porous separator materials is that junction potentials created are likely to produce misleading results (see Dohner et al, supra). Errors of 10 mV or higher can occur because junction potentials deviate from expected values.

Free diffusion type reference electrodes have been found to be free of such artifacts, but are typically very large and elaborate in construction, often requiring pumping mechanisms to maintain uni-directional flow of electrolyte. These systems are far too elaborate to be used with portable or disposable electrochemical measuring systems.

More recently, attempts have been made to solve some of these problems, particularly size reduction, by the use of a planar electrode structure such as disclosed by Lauks in U.S. Pat. No. 4,933,048. While the Lauks system successfully miniaturizes the electrode, it does suffer from several drawbacks. The Lauks device is designed to be stored in a dry non-conductive state until activated by moisture immediately prior to use. Lauks further teaches the use of a liquid permeable, ion impermeable layer to isolate the internal reference electrode from the sample environment. The liquid permeability of the layer facilitates rapid activation of the sensor by water transfer from a sample medium. The system, however, does require a wet-up period, which makes it unavailable for use during that time. Additionally, the Lauks liquid permeable configuration is subject to inaccuracies created by osmotic imbalances between reference internal and sample solutions. For example, when a sample having a lower solute concentration than that of the internal electrolyte layer is measured, osmotic pressure forces water to flow through the external membrane into the internal electrolyte layer, diluting chloride concentration (Lauks ion X) and causing reference instability. Osmotic errors might be significant when making measurements in unknown samples such as whole blood, where osmolarity of normal samples may vary by 10% or more.

Another planar reference electrode with a liquid impermeable external membrane, but complicated multi-layered system for partially exposing a salt bridge is shown by Pace in U.S. Pat. No. 4,454,007. Another planar multiple layered reference sensor has been described by Yamaguchi in U.S. Pat. No. 5,066,383.

These devices, while somewhat successful, are characterized by a very high bridge impedance which is undesirable. All these prior attempts at miniaturization of reference electrodes in a planar configuration suffer from inaccuracies associated with restrained liquid junctions.

Accordingly, it is a primary object of the present invention to provide a simple, miniaturized planar reference electrode with the accuracy of a free diffusion type junction.

Another object of the invention is to provide a reference electrode which can be stored in a conductive or ready-to-use state requiring no wet-up period.

Still another object of the present invention to provide a reference electrode having the flexibility that enables easy adjustment of internal fill solutions and bridge electrolytes by a simple procedure, in order to customize the reference potential for a particular application.

A further object of the present invention to provide an improved free diffusion junction between the reference half cell and the sensing half cell which substantially precludes undesirable ion migration between the two during an ample measurement period for a one-use, disposable electrochemical cell system.

Yet another object of the present invention to provide a new and improved, substantially solid state reference electrode including a low impedance junction between a reference electrolyte medium and a sample to be tested.

SUMMARY OF THE INVENTION

In accordance with the present invention, problems associated with the instability of the reference electrode potential are solved by the provision of a reference electrode having a controllable junction potential which also restricts ion exchange or permeability by an amount sufficient to prevent sample contamination of the reference cell fill fluid but using an essentially free diffusion low impedance junction between the sample and reference half cells. The reference electrode of the invention generally consists of an almost totally enclosed reference half-cell designed to be stored prior to use in contact with a storage solution which is externally displaced by the sample solution on which the measurements are to be performed at the time of use. The storage solution is selected to be compatible with the sample medium to be tested. The reference half cell of the invention is particularly suited to a sensor intended for disposal after a single use. Accordingly, the need to produce one accurate set of readings is stressed.

The reference electrode or half cell of the present invention is easily miniaturizable and low cost, limited in size and cost only by the efficiency of the thin or thick-film fabrication techniques. The present invention contemplates a reference electrode having a very small internal fill solution volume, in the order of microliters, which can be readily adjusted for content by equilibrating the electrode in a solution of choice for a period of minutes to hours (pre-soaking) during manufacture depending upon the geometries chosen. This provides an inherent flexibility which allows the present invention to provide an internal fill and bridge solution most suitable for intended samples.

The reference electrode of the present invention is particularly advantageous for use in the measurement of biological samples. Its optional small size allows measurements in small sample volumes; its low costs lends itself to a disposable system where the system is discarded after a single use and before accuracy becomes suspect.

The configuration associated with the preferred arrangement of the reference electrode of the present invention uses a relatively flat, possibly thick film, construction. Otherwise impervious, the system incorporates an unique hydrophilic wicking system to provide a free diffusion ionic electrical conduction between the reference and the sensing half cells which maintains both the accuracy and integrity of the reference electrode half cell during the time the cell is in use.

The reference electrode half cell of the present invention preferably consists of a planar structure in which a layer of silver (Ag) is carried on a rigid dielectric, normally ceramic, substrate. It may be formed in or covered by a patterned dielectric material to form any desired configuration. The exposed surface of the silver (Ag) is converted to or carries a further layer of silver chloride (AgCl). A layer of hydrophilic wicking material, which may be any water soluble, non-crystalline form of material that does not interfere with the desired chemistry in a carrier material, typically a gel, such as sucrose and polyvinyl alcohol (PVA), or the like, is deposited over the AgCl and dried. In certain cases, the wicking material may be entirely soluble in the storage medium outside the reference half-cell. The hydrophilic material is covered by a further dielectric liquid impermeable material, such as a liquid impermeable silicone rubber or epoxy material, which covers and seals all but a small interface area of the hydrophilic material in a manner such that the uncovered portion of the underlying hydrophilic material is left exposed to produce a free diffusion junction with the sample half cell.

The hydrophilic material can provide an immediately available free diffusion or free flow junction between the reference and sensing half cells after manufacture following the preferred method of storage. The preferred method is to store the reference half cell in an aqueous storage solution such that the water soluble components such as a polysaccharide, polyvinylpyrrolidone, or the like of the hydrophilic material dissolve into the solution, leaving a free diffusion channel. The amount of soluble matter determines the relative porosity of the system. The only limitation other than chemical compatibility is the ability of the hydrophilic wicking material to dry to a uniform non-crystalline, preferably glossy, film.

The hydrophilic wicking material preferably initially covers the entire silver/silver chloride electrode, and the exposed portion of the hydrophilic material is preferably remote from the portion covering the surface of the Ag/AgCl reference electrode itself. The thickness of the hydrophilic material and the width of the lead deposited connecting the Ag/AgCl reference electrode can be varied without affecting the junction potential of the electrode. The distance separating the exposed hydrophilic area and the Ag/AgCl electrode layer itself affects the time constant of the cell or the time that the reference electrode half cell itself remains isolated against interference from migrating chloride ions. The isolation path is configured so that accurate measurements of the species of interest can be made well before contamination occurs. The time constant, then, is a function of distance (path length) and area (path size) connecting the half cells.

The preferred reference electrode half cell of the invention is fabricated by first attaching a layer of silver, as by conventional Thin or Thick Film technology, to a rigid ceramic or other dielectric substrate material. A second layer of a dielectric optionally may be deposited over the coated substrate to adjust the exposed silver to any desired pattern. The surface of the exposed silver is then converted to present a silver chloride interface. This may be accomplished by coating the silver with a layer of silver chloride paste, electrolytically converting part of the silver layer to silver chloride or by electroless conversion of the desired amount of silver to silver chloride. The hydrophilic material, such as a sucrose and polyvinyl alcohol blend, is then deposited over the Ag/AgCl electrode pattern and allowed to air dry. The hydrophilic nature of the blend provides a continuous layer of uniform thickness upon drying in an ambient atmosphere. Components which should dry to a non-uniform crystalline state should be avoided. A final barrier layer of liquid impervious material such as an epoxy material or a silicone elastomer, such as polydimethylsiloxane, is applied over the dried hydrophilic wicking material in such a way that the predetermined desired portion of the underlying hydrophilic material is left exposed to provide the junction between the sample half cell and the reference electrode half cell. The manufactured reference half cell is preferably stored in a liquid electrolyte solution, simultaneously dissolving water soluble components of the hydrophilic layer to create a free diffusion channel and providing ions to establish a conductive path. It is preferably formulated to minimize the junction potential with an anticipated sample solution. The reference sensor is electrically conductive as stored and ready for immediate use.

DETAILED DESCRIPTION

The configuration of the reference electrode of the present invention provides very good isolation with respect to undesirable ion migration from the sample or sensing/analyzing half cell during the desired useful life of the system. While certain materials are recited herein, other metal salt electrode combinations, hydrophilic wicking materials and barrier layer may be substituted if suitable for the application at hand. The electrode system can be made any desired size and the film of any desired thickness, and the system readily lends itself to miniaturization. The system is primarily designed for use in a throw-away, disposable or one-shot portable testing device; however, it can be adapted to other uses and such are contemplated as would occur to those skilled in the art.

Figure 1:
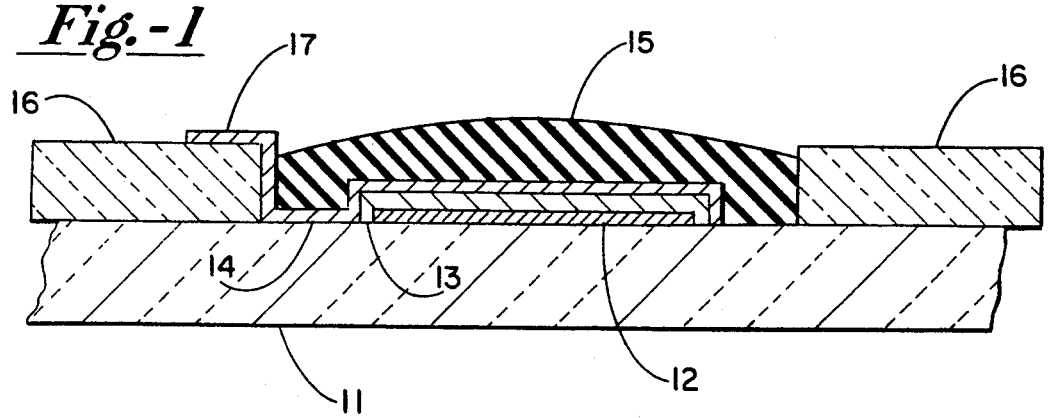
FIG. 1 is a fragmentary cross-sectional view illustrating a reference electrode with half cell fabricated in accordance with the invention.

The details of one embodiment of the invention will next be described with reference to the several drawing figures which are intended to be illustrative of the invention and not limiting as to the scope or configuration thereof in any manner. FIG. 1 illustrates a cross-section of a typical reference electrode half cell constructed in accordance with the invention and includes a ceramic or other inert substrate material 11 which carries a thin layer of metallic silver as at 12. The silver furnishes the electrical connection to an external lead associated with the electrode in a well-known manner (not shown). The silver layer is covered by a layer of silver chloride 13 which is typically formed from or on the silver layer by any of several techniques. This, in turn, is covered by a layer of chemically stable hydrophilic wicking material, typically a polysaccharide such as sucrose and polyvinyl alcohol blend, at 14. A final dielectric layer, typically an epoxy or other suitable liquid impermeable polymer material including one of many silicone rubber materials which may be cured in situ, covers the system as at 15. The system may be recessed in additional inert or insulating enclosing material, such as glass or ceramic, represented by 16. The hydrophilic wicking material 14 protrudes through beyond the dielectric covering 15 as at 17, exposing a portion of that material (FIG. 2) to the external environment. In this case, the external environment, of course, is the measurement or sample half cell (not shown). This exposed hydrophilic wicking material as at 17 provides the bridge between the reference half cell and the sensing or measurement half cell. This is the liquid junction or ionic conductor path between the half cells.

Figure 2:
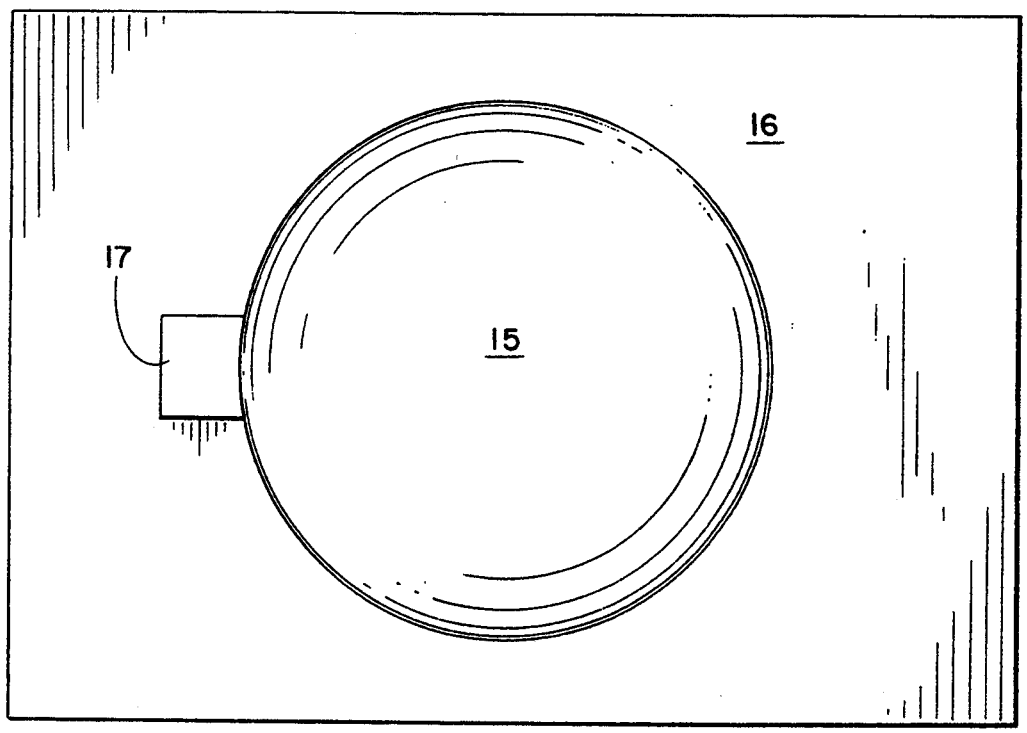
FIG. 2 represents a top view of the reference electrode of FIG. 1.

Although the system is shown in a substantially round configuration on a rectangular substrate in FIG. 2, it will be readily recognized that any desired shape and/or size may be used. Materials of construction including the reference electrode couple also may be varied according to the application of the system.

The reference electrode or half cell of the invention is typically made by depositing the layer of silver 12 on a ceramic, dielectric substrate such as $SiO_2$ or other material which may be in the form of a thin wafer using Thin or Thick Film deposition technology. The silver layer is usually between 0.0001" and 0.001" thick. A second layer of dielectric material such as glass may be applied over portions of the silver layer to thereby pattern the exposed silver layer in any desired configuration so that the size and shape of the final electrode can be adjusted as desired. The exposed surface of the silver is then converted to the silver chloride form by one of several methods. These include printing a silver chloride paste or layer over the silver layer, electrolytic conversion of the surface of the silver layer to silver chloride or electroless conversion of the desired thickness of the silver layer to silver chloride. The underlying silver layer, of course, is further utilized for the electrical connection of the electrode to external cell circuitry including the reference voltage.

The remaining preparation steps include providing the unique junction configuration of the reference electrode half cell of the invention. The AgCl layer is next covered by a solution of hydrophilic wicking material such as a polysaccharide or other water soluble benign material alone or in combination with polyvinyl alcohol (PVA) such as polyvinyl alcohol and sucrose which is deposited over the silver chloride surface and allowed to dry. As discussed above, the relative thickness of this layer along with the relative size and length of the hydrophilic wick 17 typically is adjusted for the particular application as it will determine the life expectancy of the final system during which the operation of the reference half cell will be free from outside chloride ion interference. The final layer 15 consisting of dielectric material such as a silicone rubber is applied in such a way that only a minor portion of the underlying hydrophilic material, i.e. tab 17, is left exposed as designed to connect with the sample portion of the completed cell in a well-known manner.

It is an important aspect of the invention that the size of the wick 17 and distance between the exposed hydrophilic area and the silver/silver chloride determines the time constant for the reference half cell, i.e., the time it takes for ion infiltration to occur (or the time in which the sensor is protected against chloride ion interference). The chloride ions contained in the sample or analytical sensor half cell diffuse along the hydrophilic wick 14 and eventually make their way into the reference electrode half cell and destroy the integrity of the reference Ag/AgCl concentration. The hydrophilic wicking material may be any material known to have the properties required. Although PVA and sucrose are mentioned, this is by way of example only rather than limitation, and it is believed that any of many such materials such as many types of polysaccharide materials, and other available materials may be used. Thus, according to the invention, it is through path 17, 14 that ionic conduction or a liquid exchange is established rather than through the barrier member 15.

Figure 5:
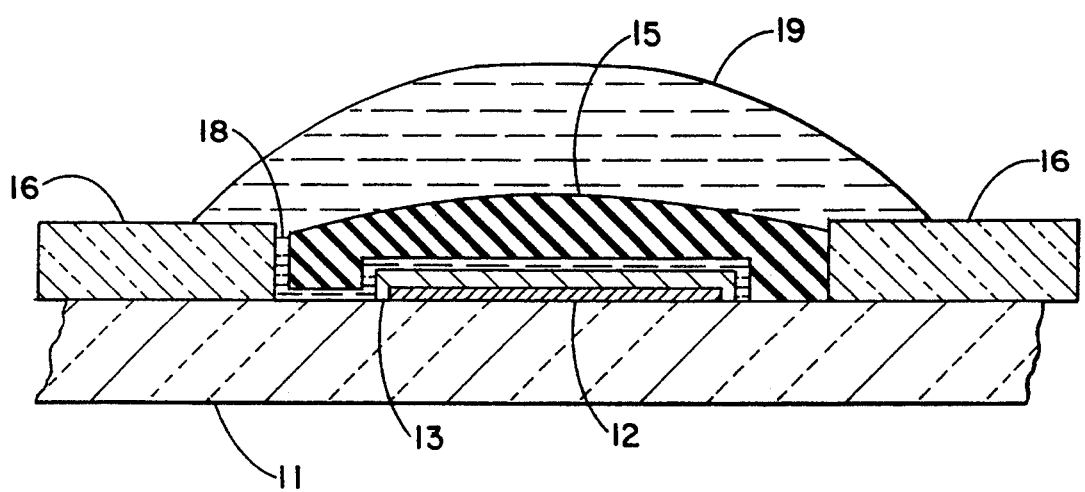
FIG. 5 is a fragmentary cross-sectional view illustrating the reference electrode of FIG. 1 as stored in contact with an aqueous storage medium.

Once manufactured, the reference electrode of the invention is preferably stored as depicted in FIG. 5. FIG. 5 shows the electrode system of FIG. 1 in contact with a liquid storage solution 19 which may be contained in combination with the electrode in any suitable manner such as in a disposable measuring cell (not shown). In the preferred arrangement, the liquid solution 19 is an electrolyte liquid which itself could serve as a calibrating solution and which is chemically compatible with the anticipated sample solution. In this manner, the ions contained in the liquid storage solution 19 both as to species and anticipated osmolarity preferably are a fairly close match with those of an anticipated sample to be measured by the cell of which the reference electrode of the invention is part.

Storage of the reference electrode in contact with the liquid solution 19 effectively dissolves the soluble portion of the layer 14 and wick 17 (FIG. 1) leaving an opening 18 between the liquid 19 and the interior of the reference electrode (FIG. 5). Liquid solution replaces the dissolved material from the layer 14, 17 thereby providing a free diffusion liquid junction between the liquid solution 19 outside the reference electrode and the electrochemical couple of the reference electrode. In this manner, when the liquid solution 19 is displaced by a sample solution, the free diffusion junction is immediately available, yet the size of the opening 18 enables a sufficient time window for accurate measurements to be made.

Thus, in accordance with the present invention, it will further be appreciated that according to the nature of the free diffusion zone created during storage of the electrode, the reference half cell will be operational and ready for immediate use with access being allowed only through the opening 18. It will further be appreciated that while the illustration of FIG. 5 depicts the opening 18 as being completely open, any combination of soluble material with, for example, PVA gel will create a partially open situation and such can be tailored to the needs of the particular application of the reference electrode.

The wet storage of the reference electrode of the invention further enables the membrane 15 to be rather rigid and liquid impermeable because it is quite unnecessary for the reference half cell to be activated or go through a wet-up period prior to use as is the case with sensors shipped or stored in the "dry" state such as that of U.S. Pat. No. 4,933,048.

Figure 3:
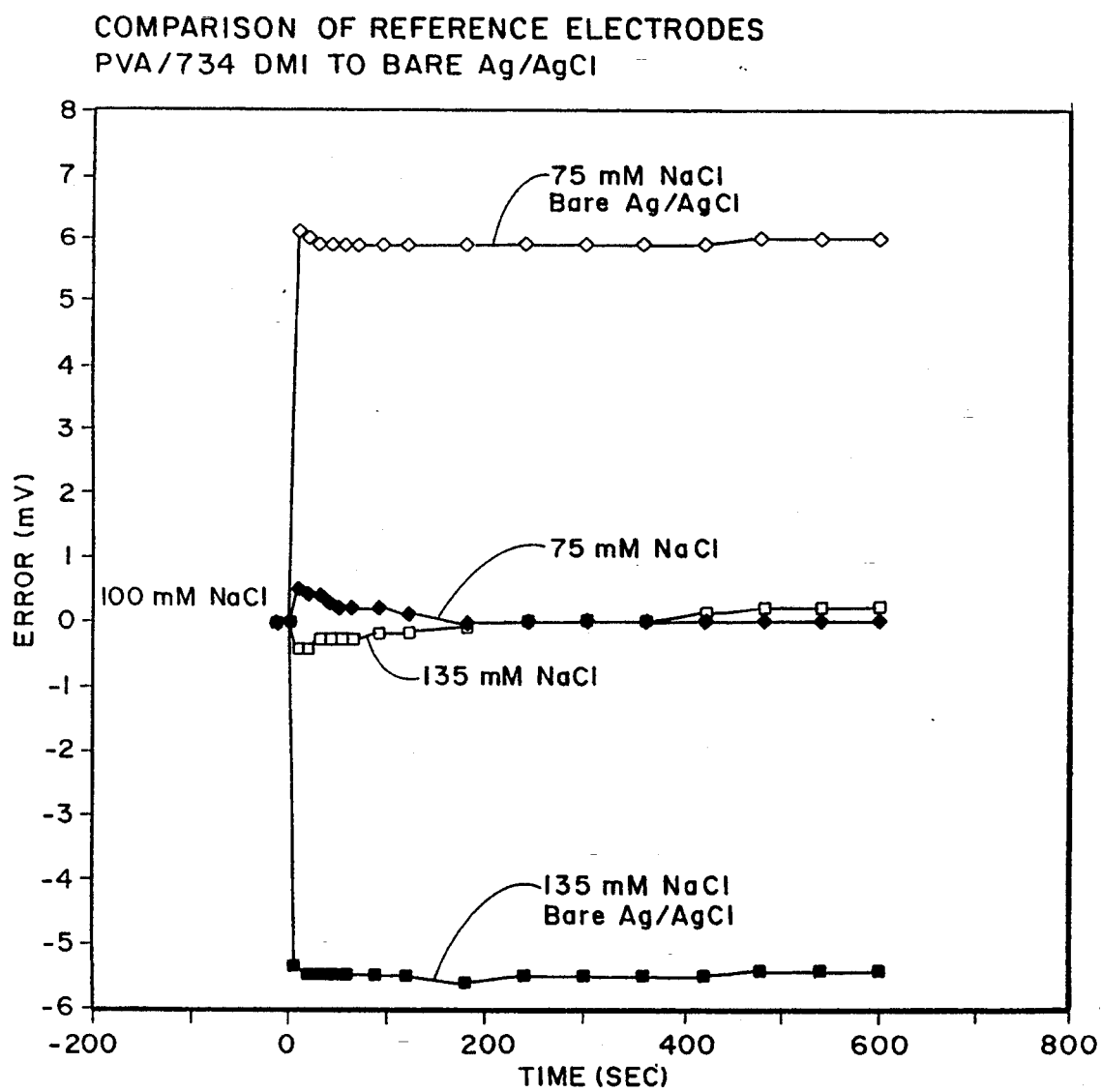
FIG. 3 is a graphical comparison of the reference electrode with bare Ag/AgCl illustrating the relative stability when exposed to salt solution.

FIG. 3 illustrates the excellent isolation achieved by the configuration of the electrode according to the invention. The exposure of bare Ag/AgCl to salt solutions (NaCl) which differ from the 100 mM isotonic solution (OV deviation) by only small amounts introduce a great amount of error in the reference electrode potential. These are illustrated by the 75 mM NaCl solution at the upper plot and the 135 mM NaCl solution at the lower curve. The center curves show the reaction of a typical cell fabricated in accordance with the invention in which initial aberrations settle out to almost zero error in about 200 seconds and show extremely close correlation up to the 600 second or 10 minute mark. This degree of accuracy is well within the normal limits of time for which the electrode would typically be useful especially if utilized as a throw-away or one-use or reference half cell.

Figure 4:
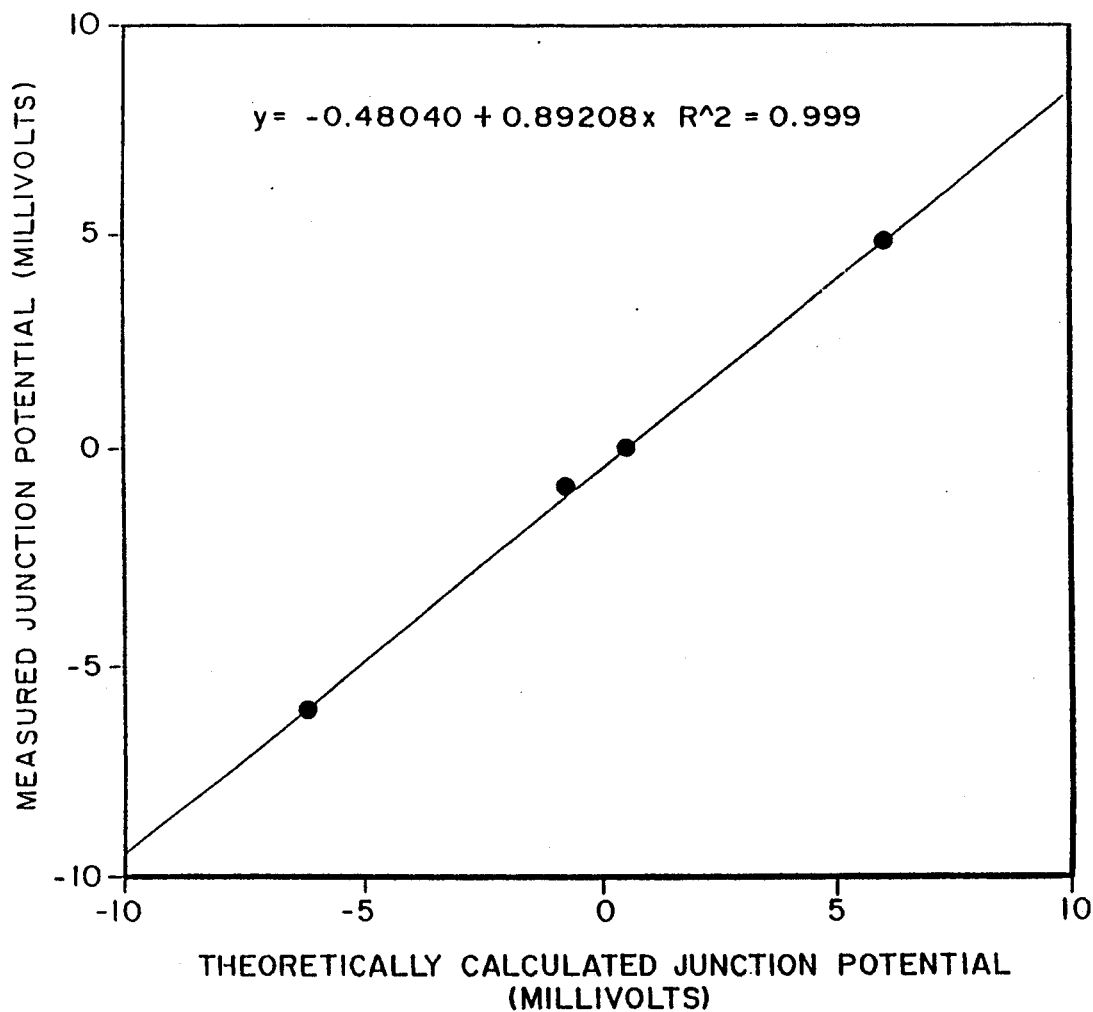
FIG. 4 is a graphical comparison of measured to calculated junction potentials, illustrating the agreement between the reference electrode and theory.

FIG. 4 represents a comparison between measured junction potentials, and theoretically derived junction potentials as calculated by the well recognized Henderson Equation. Junction potentials are created at the reference electrode and sample interface, and are a function of the electrolyte content of the sample and the reference bridge. This agreement with theory further demonstrates the accuracy of the present invention.

It can be seen that the reference electrode of the invention is one which is rather easy to manufacture and one which shows excellent isolation with respect to the protection against chloride ion interference across the potential junction. As previously described, the reference half cell of the present invention can be manufactured in any desired size and connected in accordance with well-known measuring cell techniques.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

We claim:

1. A reference electrode system which provides both a reference half cell electrical potential and a free diffusion liquid junction between a reference half cell and an analytical half cell comprising:
   (a) a dielectric substrate;
   (b) a reference half cell layer on said substrate;
   (c) an at least partially water soluble hydrophilic wicking material contacting and connecting the reference half cell and the analytical half cell and defining a passage therebetween;

(d) a dielectric, liquid impermeable barrier layer between the hydrophilic wicking material and the analytical half cell thereby essentially isolating the reference half cell except for a minor portion of the wicking material;

(e) an aqueous solution contacting and at least in part dissolving the hydrophilic wicking material creating thereby a substantially hollow, free diffusion channel in said passage by replacing dissolved hydrophilic wicking material with a solution containing dissolved wicking material; and (f) electrical connection means for connecting the reference half cell to external circuit means.

2. The apparatus of claim 1 wherein the wicking material contains at least one water soluble organic component.

3. The apparatus of claim 2 wherein the organic component is a saccharide.

4. The apparatus of claim 1 wherein the hydrophilic wicking material consists essentially of one or more water soluble components and is essentially entirely dissolved into said aqueous solution.

5. The apparatus of claim 1 wherein said reference half cell comprises a metallic layer and a layer of a salt or an oxide of the metal of the metallic layer on the metallic layer.

6. The apparatus of claim 5 wherein the metallic layer consists essentially of silver and the layer on the metallic layer consists essentially of a material selected from the group consisting of silver chloride and silver oxide.

7. The apparatus of claim 6 wherein the hydrophilic wicking material comprises polyvinyl alcohol and sucrose.

8. The apparatus of claim 6 wherein the aqueous solution is formulated to minimize the junction potential with an anticipated sample solution.

9. The apparatus of claim 8 wherein the storage electrolyte solution contains one or more chloride ion salts.

10. The apparatus of claim 1 wherein the metallic layer consists essentially of silver.

11. The apparatus of claim 1 where the substrate is selected from the group consisting of ceramic and polymeric materials.

12. The apparatus of claim 1 further comprising insulating enclosure means defining a substantially hollow volume for containing the reference half cell.

13. The apparatus of claim 1 wherein the hydrophilic wicking material comprises polyvinyl alcohol and sucrose.

14. The apparatus of claim 1 wherein the aqueous solution is a storage electrolyte solution.

15. The apparatus of claim 1 wherein the aqueous solution is formulated to minimize the junction potential with an anticipated sample solution.

16. A reference electrode system which provides both a reference half cell electrical potential and a free diffusion liquid junction between a reference half cell and an analytical half cell comprising:

(a) a dielectric substrate;
(b) a reference half cell layer on said substrate;
(c) an at least partially water soluble hydrophilic wicking material contacting and connecting the reference half cell and the analytical half cell and defining a channel therebetween wherein said wicking material is one which is at least partially leached out and replaced by a solution of leached material when exposed to an aqueous electrolyte containing solution to provide with said aqueous electrolyte containing solution an electrically conductive free diffusion liquid Junction between said reference and analytical half cells;
(d) a dielectric liquid impermeable barrier layer over the wicking material for isolating the reference half cell except for a minor portion comprising the wicking material channel left exposed; and
(e) electrical connection means for connecting the reference half cell to external circuit means.

17. The apparatus of claim 16 wherein said reference half cell comprises a metallic layer and a layer consisting of a salt or an oxide of the metal of the metallic layer on the metallic layer.

18. The apparatus of claim 17 wherein the hydrophilic wicking material comprises polyvinyl alcohol and sucrose.

19. The apparatus of claim 16 wherein the hydrophilic wicking material comprises polyvinyl alcohol and sucrose.

20. A reference electrode system which provides both a reference half cell electrical potential and a free diffusion liquid junction between a reference half cell and an analytical half cell comprising:

(a) a dielectric substrate;
(b) a conductive silver layer on said substrate;
(c) a layer of silver chloride on said silver layer;
(d) an at least partially water soluble hydrophilic wicking material including an amount of soluble saccharide contacting and connecting the silver chloride layer and the analytical half cell and defining a passage therebetween;
(e) a dielectric, liquid Impermeable barrier layer over the wicking material for isolating the reference half cell except for a minor portion defining said passage;
(f) an aqueous solution contacting and at least in part dissolving the saccharide material creating thereby a substantially hollow, free diffusion channel by replacing at least a portion of the wicking material with a solution containing the dissolved saccharine; and
(g) electrical connection means for connecting the silver layer to external circuit means.

21. The apparatus of claim 20 wherein the hydrophilic wicking material comprises polyvinyl alcohol and sucrose.

22. The apparatus of claim 20 wherein the barrier layer consists essentially of a material selected from the group consisting of epoxies and polysiloxanes.

* * * * *

UNITED STATES PATENT AND TRADEMARK OFFICE
CERTIFICATE OF CORRECTION

PATENT NO. : 5,384,031
DATED : January 24, 1995
INVENTOR(S) : Carter Anderson et al It is certified that error appears in the above-indentified patent and that said Letters Patent is hereby corrected as shown below:

In column 10, line 12, delete "Junction" and insert -- junction -- .

In column 10, line 21, before "layer" (second occurrence), insert -- salt -- .

Signed and Sealed this

Tenth Day of October, 1995

*Attest:*

BRUCE LEHMAN

*Attesting Officer*  *Commissioner of Patents and Trademarks*